(12) United States Patent
Schwartz et al.

(10) Patent No.: US 6,539,942 B2
(45) Date of Patent: Apr. 1, 2003

(54) ENDOTRACHEAL INTUBATION DEVICE

(76) Inventors: Richard Schwartz, 421 Walden Glen, Evans, GA (US) 30809; John Schwartz, 311 Turner Rd., Williamston, MI (US) 48895

( * ) Notice: Subject to any disclaimer, the term of this patent is extended or adjusted under 35 U.S.C. 154(b) by 0 days.

(21) Appl. No.: 09/837,326

(22) Filed: Apr. 19, 2001

(65) Prior Publication Data

US 2002/0153008 A1 Oct. 24, 2002

(51) Int. Cl.[7] .................... A61M 16/00; A62B 9/06
(52) U.S. Cl. ................... 128/207.14; 128/207.15; 128/207.16; 606/108
(58) Field of Search ................. 128/207.14, 207.15, 128/207.16, 207.17, 200.16; 606/108

(56) References Cited

U.S. PATENT DOCUMENTS

| | | | |
|---|---|---|---|
| 2,975,785 A | | 3/1961 | Sheldon |
| 3,162,214 A | | 12/1964 | Bazinet, Jr. |
| 3,470,876 A | * | 10/1969 | Barchilon |
| 4,236,509 A | | 12/1980 | Takahashi et al. |
| 4,353,358 A | * | 10/1982 | Emerson ............... 600/139 |
| 4,589,410 A | * | 5/1986 | Miller ............... 128/207.15 |
| 4,669,172 A | | 6/1987 | Petruzzi |
| 4,846,153 A | | 7/1989 | Berci |
| 4,905,666 A | | 3/1990 | Fukuda |
| 4,949,716 A | | 8/1990 | Chenoweth |
| 5,203,320 A | | 4/1993 | Augustine |
| 5,456,250 A | * | 10/1995 | Hissong ............... 128/200.26 |
| 5,520,222 A | | 5/1996 | Chikama |
| 6,053,166 A | * | 4/2000 | Gomez ............... 128/200.26 |

FOREIGN PATENT DOCUMENTS

| | | |
|---|---|---|
| JP | 5329095 | 12/1993 |
| WO | WO 91/12044 | 8/1991 |

* cited by examiner

*Primary Examiner*—Aaron J. Lewis
*Assistant Examiner*—Darwin P. Erezo
(74) *Attorney, Agent, or Firm*—Richard C. Litman

(57) ABSTRACT

A device for facilitating intubation including an elongate tube inserted in a conventional endotracheal tube. An imaging device (e.g., a nasopharyngoscope) is inserted through the device, and the device is then inserted through an endotracheal tube. The device includes a control wire and handgrip to curve the distal end of the device into an L-shaped configuration, which is produced via a series of interlinked, truncated ring-like elements disposed along the distal portion of the tube. The amount of force applied to the handgrip controls the degree of bend in the distal end of the device. The L-shaped configuration facilitates the proper visualization of the vocal cords by the imaging device.

14 Claims, 3 Drawing Sheets

ENDOTRACHEAL INTUBATION DEVICE

BACKGROUND OF THE INVENTION

1. Field of the Invention

The present invention relates generally to intubation and, more specifically, to an improved endotracheal intubation device through which an imaging device (e.g., a nasopharyngoscope) is inserted and manipulated to facilitate an endotracheal intubation procedure.

2. Description of the Related Art

A number of medical devices have been devised to assist with the intubation of the trachea during emergency or operative medical procedures. Typically, intubation of the trachea is required in the emergency setting to: prevent aspiration of gastric contents into the lungs; provide an adequate airway to the lungs; therapeutically alter the level of $CO_2$ in the blood stream; and provide anesthetic gases to patients in the operating room. Problems with the technique are that, often, intubation is neither easy nor non-traumatic for the patient. Several factors contribute to the problem. First, there are many variations in the length of the trachea among patients. Second, once the tube is inserted, the device is difficult to manipulate and/or adjust due to limited flexibility in the medical instrument. Third, the trachea is often difficult to visualize due to anatomic variabilities such as anterior larynx, inability to open mouth, decreased neck mobility (may be secondary to spinal immobilization or anatomy), etc.

In performing an intubation procedure, an instrument, i.e., a laryngoscope, is first introduced into the patient's mouth, and the tongue of the patient is elevated so that the patient's vocal cords and epiglottis can be clearly identified. In practice, the medical practitioner can find this difficult to accomplish because of physical and anatomical variations among patients. Thus, the practitioner is often left to rely on prior experience or "blind faith" with a touch or feel technique. This can be harmful to the patient, especially as to proper identification of the patient's vocal cords.

While the length of the trachea for individual patients is usually classified by a patient's teeth-bifurcation distance, there is no absolute standard. Thus, there is a need for a medical instrument which provides access to the vocal cords without the hazards associated with conventional art devices. It is desired to provide a medical device which utilizes an untethered flexible tubular endotracheal device and sheath that flexes into a L-shape, for accessing the vocal cords under the direct visualization of an enclosed imaging device (e.g., a nasopharyngoscope). The instant invention answers the need.

U.S. Pat. No. 2,975,785 issued to Sheldon discloses an optical viewing instrument comprising an endoscope sheath and a plurality of tube elements arranged in an end to end relationship. One end of the sheath is secured to a control housing and has its interior end in communication with the interior chamber of the housing. The control housing serves to support various control structures for the endoscope, and includes two mating castings and a plurality of cables which are secured to a terminal end of the sheath with the other ends of the cables secured and looped around a pair of pulleys positioned within the chamber. The optical system consists of a flexible bundle of optically aligned transparent glass fibers which are secured by a pair of clamps. Each of the glass fibers of a bundle of this sort transmits light from one end by multiple internal reflections within the fiber. The bundle size of the fibers limits the overall flexibility of the instrument.

U.S. patents issued to Bazinet (U.S. Pat. No. 3,162,214), Takahashi et al. (U.S. Pat. No. 4,236,509) and Petruzzi (U.S. Pat. No. 4,669,172) disclose flexible tubular structures composed of coiled wire and/or tethered circular ring elements which provide for more flexibility in the use of an inserted endoscope. Petruzzi discloses a method for fabricating a flexible shaft comprising a spiral cut member having an essentially uniform inside diameter and a tapered linear profile coextensive with at least a portion of the spiral cut member. This flexible shaft is fabricated initially by progressively removing a portion of the exterior wall along a segment of a relatively rigid tube thereby forming a substantially tapered profile.

While the shapes and contours of the aforementioned tubular structures have added flexibility in the use of endoscopes, bending devices coupled thereto have proven advantageous to extend flexibility and control of flexibility. For example, patents respectively issued and granted to Fukuda (U.S. Pat. No. 4,905,666), Chikama (U.S. Pat. No. 5,520,222) and Ogino (JP 5,329,095) teach bending devices which use tethers linked to the tubular structures via pulleys or chain driven winding mechanisms. These features add to the complexity of the device, and are prone to mechanical failure, rendering the endoscopic device inoperable.

U.S. Pat. No. 4,861,153 issued to Berci discloses an intubating video endoscope which includes an elongated sheath member with a selectively controllable bendable section housing an image forming optical system. A generally rigid section includes a control housing. An image transmitting optical system extends throughout the length of the sheath member and terminates behind and adjacent to the image forming system. A light transmitting system also extends throughout the length of the sheath member to the image forming optical system, the rearward end of which is adapted to be operatively connected to a light source. A channel, extending through out the length of the sheath member, provides a flow of pressurized gas which is directed across the image forming optical system to keep the image forming optical system operationally clear.

U.S. Pat. No. 4,949,716 issued to Chenoweth discloses a hand held medical device with a wide range of nasally placed airway tubes to afford better control of airway tubes. A soft flexible manipulator containing a spring controls the airway tube. A stethoscope headset provides an audible reference for guiding the airway tube, and affords an additional reference to confirm the proper placement of the airway tube. An endotracheal device having similar features is disclosed in the PCT application of Adair (WO 91/120044), except that the handle has an oxygen supply conduit for supplying oxygen to the patient during the intubation process.

None of the above inventions and patents, taken either singularly or in combination, is seen to describe the instant invention as claimed. Thus a endotracheal intubation device solving the aforementioned problems is desired.

SUMMARY OF THE INVENTION

The invention is a device to facilitate intubation, the device having a hand-grip control mechanism for selectively controlling the amount of curvature at the distal end of the device. The device is inserted into a conventional endotracheal tube. A conventional imaging device, e.g., a nasopharyngoscope, is inserted centrally through the device. The device is formed into an L-shaped position by the handgrip. This L-shaped position facilitates proper visualization of the vocal cords.

The L-shaped configuration is produced via a series of interlinked and truncated ring like elements disposed along the distal portion of the tube. A wire passing through the tube from the interlinked rings to the handgrip activates the L-shaped configuration. The amount of force applied to the handgrip controls the degree of bend in the distal end of the device. A standard nasopharyngoscope is inserted through the center of the device, and the device is then inserted into a standard endotracheal tube. The tip of the nasopharyngoscope extends to or just beyond the end of the endotracheal tube which allows an operator to visualize the vocal cords. This allows proper intubation without damaging the vocal cords.

Once the tube combination is in place in the patient, the handgrip is released to relax the L-shaped configuration and the device including the scope is removed, leaving the tube in place. In a preferred embodiment, the device is made of a lightweight stainless steel material. It can be made from a variety of materials including surgical grade plastics. Thus, the device could be partially or wholly disposable.

Accordingly, it is a principal object of the invention to provide an improved endotracheal intubation device for imaging internal portions of a person's airway passages to assist in endotracheal intubation.

It is another object of the invention to provide an improved endotracheal intubation device which facilitates safe navigation through the trachea of a patient during intubation.

It is a further object of the invention to provide an improved endotracheal intubation device with a hand-gripping mechanism for easily conforming the device to an L-shaped configuration.

Still another object of the invention is to provide an improved endotracheal intubation device which is inserted into a conventional endotracheal tube, and through which is inserted a conventional nasopharyngoscope, to facilitate a safe intubation procedure.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is directed to an improved endotracheal intubation device for intubating a patient with an endotracheal tube, which is used for inserting and manipulating the tube and medical imaging devices (i.e. endoscopes, nasopharyngoscopes, laryngoscopes, etc.). A preferred embodiment of the present invention is shown in FIGS. 1–3, and is generally referenced by numeral 4.

Figure 1:
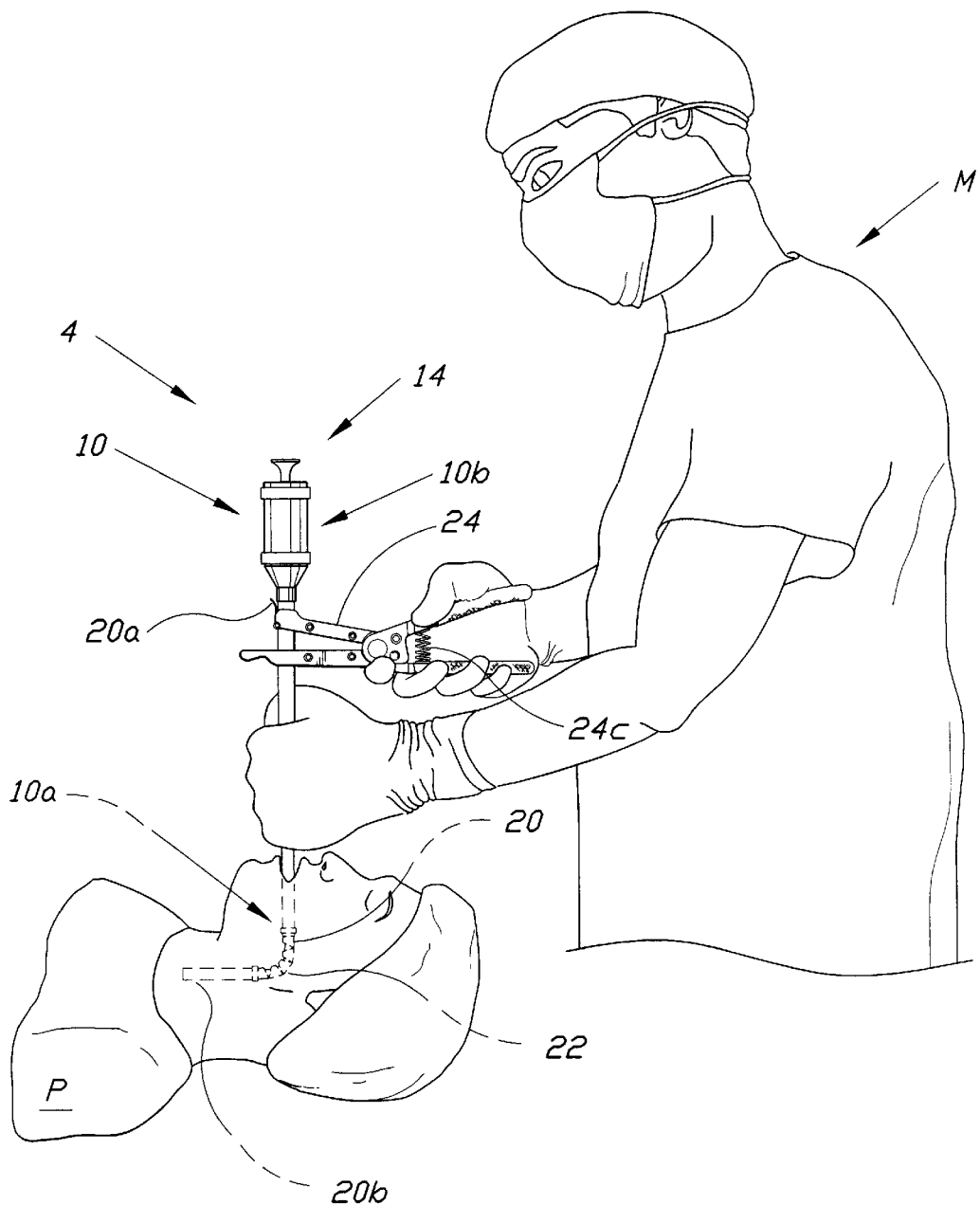
FIG. 1 is an environmental, perspective view of an endotracheal intubation device according to the present invention.

As best seen in FIG. 1, the improved endotracheal device 4 is shown manipulated by a medical practitioner M. The endotracheal intubation device 4 comprises an improved tubular body 10. The device is inserted through a conventional endotracheal tube 4a. The tubular body 10 has an actuator in the form of a hand-grip control mechanism 24 mounted thereto for selectively controlling the amount of curvature at the distal end 10a of the body 10, and a holder for an eye piece 14 of the nasopharyngoscope on a top portion 10b of the body 10.

The distal end 10a is formed into an L-shaped position when fully activated by the handgrip 24. This L-shaped position (when activated) facilitates the proper visualization of the vocal cords via the nasopharyngoscope inserted through the device. The L-shaped configuration is produced via a series of inter-linked and truncated ring like elements 20 along the distal portion of the device. The L-shaped configuration is activated by a wire 20a attached to the actuator and extending from a jaw of the handgrip control mechanism 24 and passing through the device to the first interlinked ring 20b. The amount of force applied to the hand-grip 24 forces the actuator up, thereby tensioning the wire 20a which is connected to the last interlinked ring 20b, thereby controlling the degree of bend in the distal end 10a of the device 4.

Figure 2:
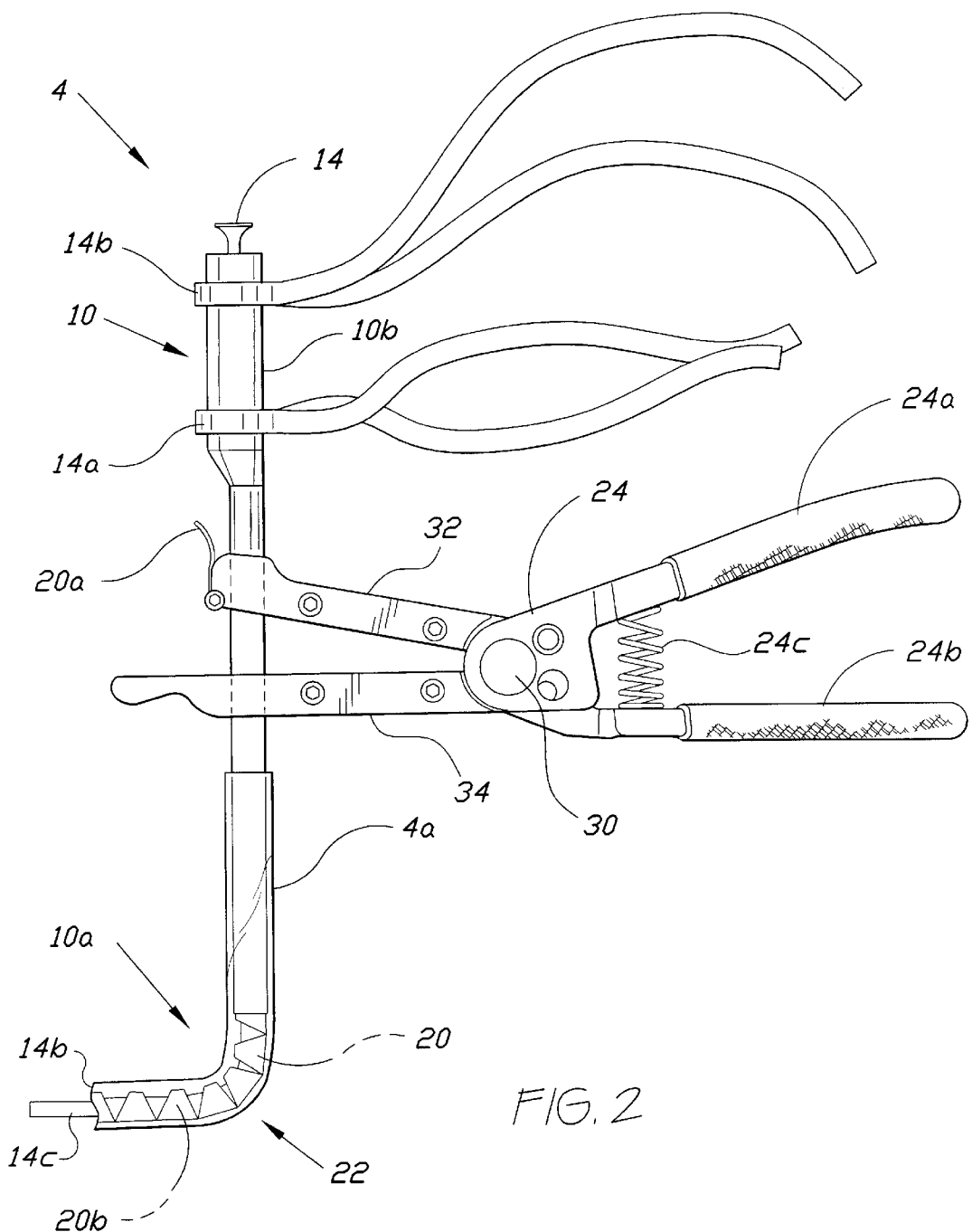
FIG. 2 is a perspective view of the endotracheal intubation device, illustrating an L-shaped configuration according to the invention.
Figure 3:
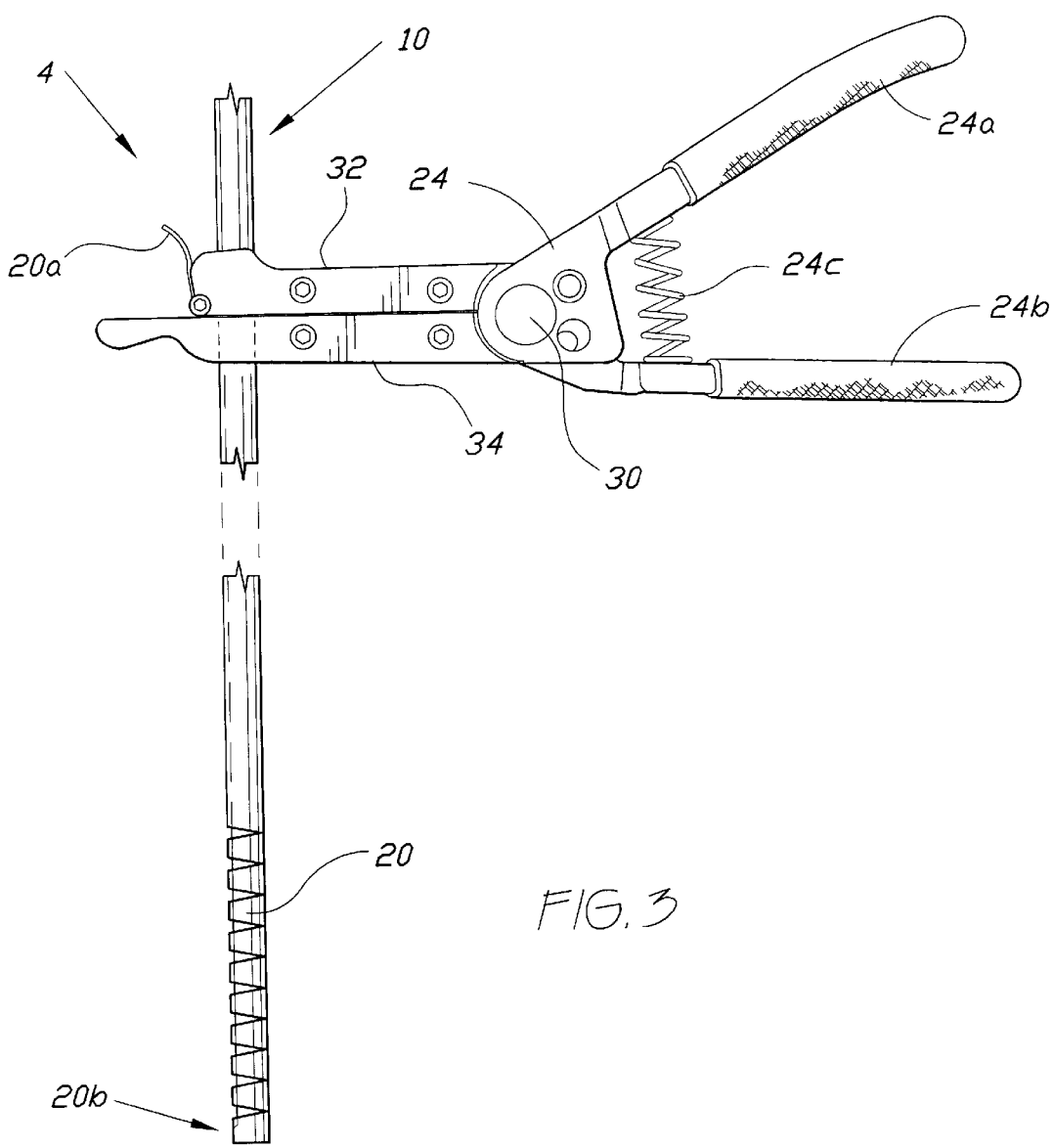
FIG. 3 is a perspective view of the endotracheal intubation device according to the invention, illustrating the device in a relaxed, linear, unflexed condition.

As best seen in FIG. 2, the eye piece holder 10b is a half cylinder with a diameter and length that allows the nasopharyngoscope eye piece 14 to be held securely in place, with small straps 14a and 14b that wrap around and are attached to the holder 10B (in FIG. 2). Straps 14a, 14b could have hook and loop fastener portions, or other conventional fasteners.

The handgrip 24 allows medical practitioner M to produce the L-shaped configuration 22 as shown in FIGS. 1 and 2. The L-configuration 22 of the distal end operatively serves to allow the practitioner M to visualize a patient's vocal cords with an enclosed fiberoptic scope. This facilitates the intubation with only a minimal requirement for the mouth of the patient P to be opened; the mouth is only required to opened to the external dimension of the endotracheal tube itself. Additionally, this technique will minimize the amount of laryngeal manipulation (and trauma) required, when compared to standard laryngoscopy. The handgrip 24 includes handles 24a and 24b and jaws 32 and 34 pivotally connected by pivot pin 30 with spring 24c disposed between handles 24a and 24b. The handles 24a and 24b also give the practitioner M a good solid grip for manipulating the device 4 with a high degree of accuracy in positioning the endotracheal tube without slippage.

As diagrammatically illustrated in FIG. 3, the improved endotracheal device 4 is shown in a relaxed state whereby the hand grip 24 has been released to provide for easy removal or further penetration once the body 10 has been inserted a predetermined distance within the trachea of a patient P. In this configuration, the activated force provided by the flexing means or hand grip mechanism 24 is virtually a zero. In this configuration, the device 4 and the nasopharyngoscope 14 are removed from the endotracheal tube, leaving the tube 4a in the desired position in the patient.

In use, and as best seen in FIG. 2, a standard nasopharyngoscope 14 is placed in the center of the tubular body 10. The device 4 with the nasopharyngoscope 14 is then inserted into a standard endotracheal tube 4a, such that the fiberoptic end 14c of the nasopharyngoscope extends just to or just beyond the end 4b of the endotracheal tube 4a. The tube-sheath-nasopharyngoscope combination is inserted into the patient's mouth and pharynx, and the flexing mechanism 24 is used to flex the device 4 into the L-configuration 22 to better visualize the patient's vocal cords, via the nasopharyngoscope 14, of course.

After the tube has been inserted past the vocal cords, the flexing hand grip 24 may be relaxed while the tube is inserted farther. The hand-grip mechanism 24 can include spring loaded features such as compression spring 24c (best seen in FIG. 3) which allows biasing of hand-grip portions 24a and 24b, respectively. After the endotracheal tube 4a is in place, the device 4 and nasopharyngoscope 14 may be removed. With the balloon cuff on the standard endotracheal tube inflated, the patient P may be ventilated in the conventional fashion.

Other advantages of the improved endotracheal intubation device 4 according to the invention are as follows. The body 10 is made of lightweight stainless steel material, in a preferred embodiment. Or, a variety of materials could be employed to make the device, including surgical grade plastics. Thus, the device could be partially or completely disposable. The type of medical instrument 14 used with the device is not limited to a pharyngoscope; endoscopes, laryngoscopes and other fiberoptic scopes or an incorporated fiberoptic bundle/eye piece/light-source combination can be employed. The device may be made in various sizes, in view of the wide range of patient anatomical characteristics discussed above.

It is to be understood that the present invention is not limited to the embodiments described above, but encompasses any and all embodiments within the scope of the following claims.

We claim:

1. A device to facilitate endotracheal intubation, comprising:
   a substantially tubular element having first and second portions, said first portion having a proximal attachment section for attachment of an imaging device thereto, said second portion having a distal portion and a terminal end;
   said distal portion comprising a series of interconnected ring elements of predetermined ring thickness, and having shaped spaces therebetween, such that said interconnected ring elements form a channel therethrough, there further being a first ring element at said second portion terminal end;
   a handgrip control mechanism attached to said second portion below the junction between said first and second portions, the handgrip control mechanism having first and second handles, first and second jaws, and a pivot pin pivotally connecting the first and second handles and first and second jaws; and
   a control wire having first and second ends, with the first control wire end attached to the first ring element, and the second control wire end attached to the first jaw of the handgrip control mechanism, the wire passing entirely through said second portion;
   wherein manipulation of said control grip causes the first and second jaw to separate, the first jaw pulling said control wire to close said shaped spaces between said ring elements, thus to flex said second portion distal end into a generally L-shaped configuration, in a controlled manner from fully straight to fully L-shaped.

2. The device to facilitate endotracheal intubation according to claim 1, wherein the device is dimensioned and configured to have an optical imaging device inserted entirely therethrough.

3. The device to facilitate endotracheal intubation according to claim 1, wherein the device is made of stainless steel.

4. The device to facilitate endotracheal intubation according to claim 1, further comprising an endotracheal tube disposed about the second portion of said tubular element, wherein said tubular device is removed from the endotracheal tube after the endotracheal tube is positioned in a patient.

5. The device to facilitate endotracheal intubation according to claim 1, wherein said series of interconnected ring elements comprises a plurality of interlinked asymmetric ring elements.

6. The device to facilitate endotracheal intubation according to claim 1, further comprising a spring disposed between said first and second handles.

7. An endotracheal intubation assembly, comprising:
   an endotracheal tube;
   an imaging device; and
   a device for facilitating endotracheal intubation having:
      a substantially tubular element having first and second portions, said first portion having a proximal attachment section for attachment of said imaging device thereto, said second portion having an exterior, a distal portion and a terminal end;
      said distal portion comprising a series of interconnected ring elements of predetermined ring thickness, and having shaped spaces therebetween, such that said interconnected ring elements form a channel therethrough, there further being a first ring element at said second portion terminal end;
      a handgrip control mechanism attached to said second portion below the junction between said first and second portions; and
      a control wire having first and second ends, with the first control wire end attached to the first ring element, and the second control wire end attached to the handgrip control mechanism;
   wherein the imaging device is attached to the first portion of the tubular element and extends through the second portion of the tubular element, the endotracheal tube being disposed about the exterior of second portion of the tubular element; and
   wherein manipulation of said control grip causes said control wire to close said shaped spaces between said ring elements, thus to flex said second portion distal end into a generally L-shaped configuration, in a controlled manner from fully straight to fully L-shaped in order to visualize a patient's vocal chords during endotracheal intubation, the imaging device and the device for facilitating insertion being removed from the endotracheal tube after the endotracheal tube is positioned in a patient.

8. The endotracheal intubation assembly according to claim 7, wherein said handgrip control mechanism further comprises:
   first and second handles;
   first and second jaws; and
   a pivot pin pivotally connecting the first and second handles and first and second jaws.

9. The endotracheal intubation assembly according to claim 8, further comprising a spring disposed between said first and second handles.

10. The endotracheal intubation assembly according to claim 7, wherein the device for facilitating endotracheal intubation is made of stainless steel.

11. The endotracheal intubation assembly according to claim 7, wherein said endotracheal tube is made of a plastics material, at least in part.

12. The endotracheal intubation assembly according to claim 7, wherein said series of interconnected ring elements comprises a plurality of interlinked asymmetric ring elements.

13. A device for facilitating endotracheal insertion in combination with an endotracheal tube, comprising:
   an endotracheal tube;
   an endotracheal tube insertion device having:
      a substantially tubular element having first and second portions, said first portion having a proximal attachment section for attachment of an imaging device thereto, said second portion having an exterior, a distal portion and a terminal end;
      said distal portion comprising a series of interconnected ring elements of predetermined ring thickness, and having shaped spaces therebetween, such that said interconnected ring elements form a channel therethrough, there further being a first ring element at said second portion terminal end;
      a handgrip control mechanism attached to said second portion below the junction between said first and second portions, the handgrip control mechanism having first and second handles, first and second jaws, and a pivot pin pivotally connecting the first and second handles and first and second jaws; and
      a control wire having first and second ends, with the first control wire end attached to the first ring element, and the second control wire end attached to the first jaw of the handgrip control mechanism, the wire passing entirely through said second portion;
   wherein said endotracheal tube is disposed about the exterior second portion of the tubular element, the tubular element being dimensioned and configured for insertion of an imaging device therethrough; and
   wherein manipulation of said control grip causes the first and second jaw to separate, the first jaw pulling said control wire to close said shaped spaces between said ring elements, thus to flex said second portion distal end into a generally L-shaped configuration, in a controlled manner from fully straight to fully L-shaped in order to visualize a patient's vocal chords during endotracheal intubation, the insertion device being removed from the endotracheal tube after the endotracheal tube is positioned in a patient.

14. The device for facilitating endotracheal insertion according to claim 13, further comprising a spring disposed between said first and second handles.

\* \* \* \* \*